United States Patent [19]

Fukuda et al.

[11] Patent Number: 5,331,091
[45] Date of Patent: Jul. 19, 1994

[54] MELANIN FORMATION-INHIBITORY PROTEIN, AND ITS PREPARATION AND USES

[75] Inventors: Shigeharu Fukuda; Yasuo Suemoto; Masashi Kurimoto, all of Okayama, Japan

[73] Assignee: Kabushiki Kaisha Hayashibara Seitbutsu Kagaku Kenkyujo, Okayama, Japan

[21] Appl. No.: 109,249

[22] Filed: Aug. 20, 1993

[30] Foreign Application Priority Data

Aug. 21, 1992 [JP] Japan ................. 4-264025

[51] Int. Cl.⁵ .................. C07K 3/02; C07K 3/28; C12P 21/02; A61K 37/43
[52] U.S. Cl. ................. 530/350; 435/70.3
[58] Field of Search ............ 530/350, 395; 435/70.3; 514/21, 8

[56] References Cited

U.S. PATENT DOCUMENTS

| | | | |
|---|---|---|---|
| 4,276,282 | 6/1981 | Sugimoto et al. | 424/85.7 |
| 5,077,059 | 12/1991 | Mishima et al. | 424/573 |
| 5,214,028 | 5/1993 | Tomita et al. | 514/6 |

FOREIGN PATENT DOCUMENTS 5654158  8/1977  Japan .

OTHER PUBLICATIONS

Multiple Molecular Farms of Human Lactoferrin Furmanski et. al. J. Exp. Med. 170: Aug. 1989 415-429.
Ando, S., et al., *Natural Human Interferon-Derived form Lipopolysaccharide-stimulated Human Myelomonocytic HBL-38 Cells,* Japan J. Cancer Research, vol. 79, Jun. 1988, pp. 757-765.
Kreutzfild, K. L., et al., *Effects of a Ventrally Localized Inhibitor of Melaninization on Cultured S91 and B16 Mouse Melanoma.* Pigment Cell Research, vol. 2, 1989, pp. 123-125.
Laemmli, U. K., *Cleavage of Structural Proteins during the Assembly of the Head of the Bacteriophage T4.* Nature vol. 227, Aug. 15, 1970, pp. 680-685.
Imokama, Genji and Mishima, Yukata, *Loss of Melanogenic Properties in Tyrosinases Induced by Glycosylation Inhibitors within Malignant Melanoma Cells.* Cancer Research, vol. 42, May 1982, pp. 1994-2002.
Muller, Gunter et al., *Functional analysis of alternatively spliced tyrosinase gene transcripts.* Embo Journal, vol. 7, 1988, pp. 2723-2730.
Maruzen Co., Ltd., *Labomanual Genetic Enginnering.* Tokyo, Japan, 1988.
Ito et al., *Microanalysis of Eumelanin and Pheomelanin in Hair and Melanomas by Chemical Degradation and Liquid Chromatography.* Analytical Biochemistry, vol. 144, 1985, pp. 527-536.
Hamada et al., *Intracellular Localization of Tyrosinase Inhibitor in Amelanotic and Melanotic Malignant Melanoma.* British Journal of Dermatology, vol. 86, 1972, pp. 385-394.

*Primary Examiner*—Jeffrey E. Russel
*Assistant Examiner*—Nancy J. Gromet
*Attorney, Agent, or Firm*—Browdy and Neimark

[57] ABSTRACT

A novel melanin formation-inhibitory protein, which has a molecular weight of 90,000±20,000 and a pI of 5.5±0.5, exerts a tyrosinase formation-inhibitory activity in pigment cells but does not substantially inhibit the inherent tyrosinase activity. Thus, the protein is advantageously used as a pharmaceutical and as a cosmetic in the prevention and/or treatment for local chromatosises such as chloasma, ephelis and sunburn, as well as for systemic chromatosises such as addisonism.

9 Claims, 1 Drawing Sheet

MELANIN FORMATION-INHIBITORY PROTEIN, AND ITS PREPARATION AND USES

BACKGROUND OF THE INVENTION

1. Field of the Invention

The present invention relates to a protein, and its preparation and uses. More particularly, the present invention relates to a novel protein, and has a melanin formation-inhibitory activity which is derived from a human cell, and additionally, relates to the preparation and use of this novel protein.

2. Description of the Prior Art

Melanin is present in the skin and plays an important role in with protecting the body from the harmful effects of ultraviolet rays. Melanin is also an important factor in medical science and cosmetology. It is known that melanin is formed or synthesized in skin tissues. Excessive amounts of melanin darkens the skin, and the nonuniform distribution of melanin causes chloasma and ephelis, both of which are skin disorders. Conventionally, tyrosinase inhibitors such as vitamin C, glutathione and cysteine have been used to decrease the level of melanin in the skin and thereby producing a lightly pigmented skin.

These tyrosinase inhibitors are, however, unfavorably stable and inadequate in their skin-whitening effect on viable cells. Although Hydroquinone and monobenzyl ether of hydroquinone (MBEH), which have been used as a tyrosinase inhibitor, are highly effective in achieving lightly pigmented skin, they destroy the inherent physiological functions of the skin and cause side effects such as alphos, pigmentary disorder and contact dermatitis. in *Pigment Cell Research*, Vol. 2, pp. 123–125 (1989), K. L. Kreutzfeld et al. studied the question of why ventral skin-tissues of frogs are whiter than the dorsal skin-tissues, by attempting to extract a melanin formation-inhibitory substance from the ventral skin-tissues. They reported that a protein having a molecular weight of about 300,000 was found to have melanin formation-inhibitory activity. However the protein is, of frog origin and thereby presents a limitation in its use for lightening skin color in humans.

SUMMARY OF THE INVENTION

As explained above, there is great demand for developing a skin-whitening agent that is both safe and effective for human use. The present invention provides a composition which is effective in lightening dark skin and in the treatment of chloasma and ephelis, as well as having satisfactory safety and purity with relatively-high specific activity. The present invention also establishes a preparation of a protein having melanin formation-inhibitory activity and which is derived from a human cell. Moreover the present invention provides a novel technique useful in studying the mechanism of melanin formation.

The present inventors studied melanin formation-inhibitory substances that are produced by established human cell lines and, As a result, purified and recovered a melanin formation-inhibitory protein from a culture supernatant of an established human cell line by using sequential chromatographic techniques. The present inventors studied the physicochemical properties of the protein establishing its preparation, and found had that it a melanin formation-inhibitory activity. Thus, the present inventors accomplished this invention. The present protein having a melanin formation-inhibitory activity has the following physicochemical properties:

(1) Molecular weight
90,000±20,000 on sodium dodecyl sulfate polyacrylamide gel electrophoresis (SDS-PAGE);

(2) Isoelectric point
pI=5.5±0.5;

(3) Ultraviolet absorption spectrum
Exerting the maximum absorption spectrum at a wavelength of around 280 nm;

(4) Solubility in solvent
Soluble in water, physiological saline, phosphate buffer and Tris-HCL buffer;

(5) Activity
Exerting a melanin formation-inhibitory activity in pigment cells;

(6) Stability of activity
Inactivated in water (pH 7.4) at 80° C. for 30 minutes; Stable in water (pH 7.4) at 4° C. for one month.

BRIEF DESCRIPTION OF THE ACCOMPANYING DRAWINGS

DETAILED DESCRIPTION OF THE INVENTION

Figure 1:
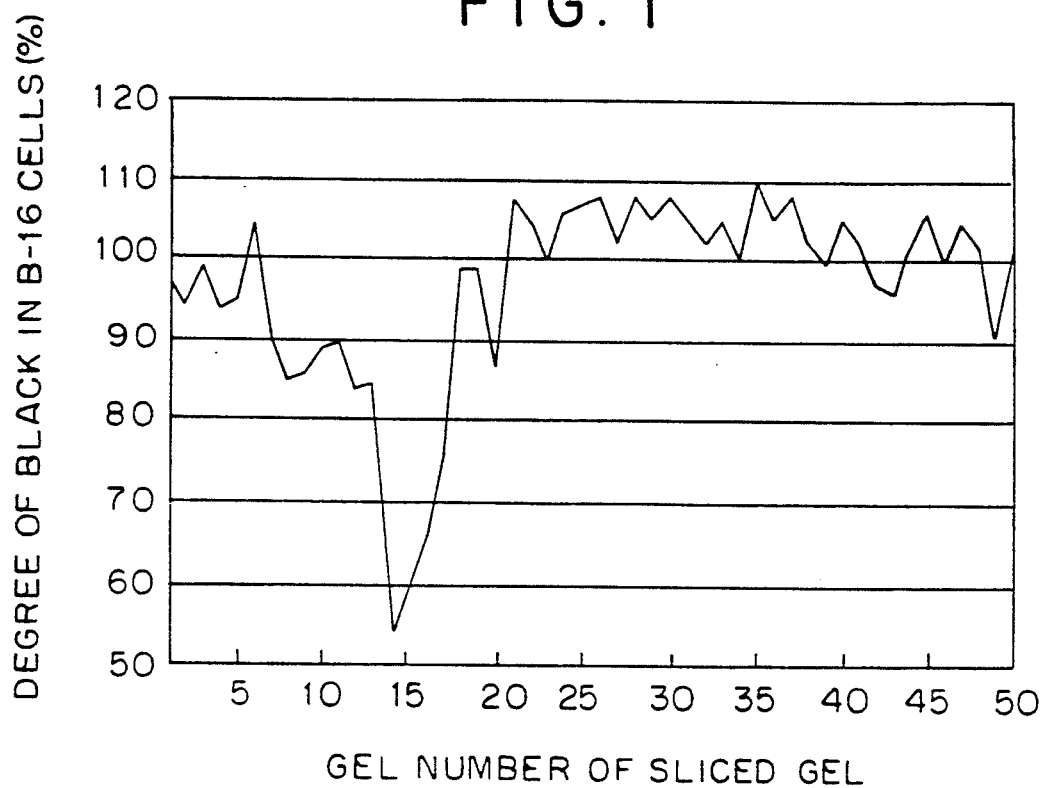
FIG. 1 shows an SDS-PAGE pattern of the present melanin formation-inhibitory protein.

The preparation of melanin formation-inhibitory protein according to the present invention is achieved by allowing an inducer to act on human cells such as leukocytes, lymphocytes and established cell lines capable of producing the protein. The established human cell lines that can be used in the invention are, for example, myelomonocytic cell lines such as HL-60 cells (ATCC CCL 240 ), U937 cells ( ATCC CRL 1593) and HBL-38 cells as described in *Japanese Journal of Cancer Research*, Vol. 79, pp. 757–765 (1988); T-cells such as HPB-MLT (FERM BP-2430); and B-cells such as RAMOS cells (ATCC CRL 1596), all of which give a sufficiently high production level of the present protein. The methods for proliferating such a human cell line in the invention are in vitro and in vivo proliferations. The in vivo proliferation, as described in Japanese Patent Publication No. 54,158/81, where cells to be proliferated are transplanted into a non-human warm-blooded animal, can be employed in the invention as an in vivo proliferation. By using this in vivo proliferation, a large amount of cells is readily prepared.

The following experiments describe the present invention in detail.

EXPERIMENT 1

Preparation and Physicochemical Properties of Protein Having Melanin Formation-Inhibitory Activity New born hamsters were injected with antiserum, prepared from rabbits in a conventional manner, to decrease their immunoreaction, and subcutaneously transplanted with HPB-MLT cells (FERM BP-2430), and they bred for 3 weeks in usual manner. Tumors, formed subcutaneously in hamsters, were extracted, cut into pieces, and then suspended and dispersed in physiological saline. The resultant cells were washed with serum-free RPMI 1640 medium (pH 7.2), and resuspended in the same fresh medium to give a concentration of about $5 \times 10^6$ cells/ml. One µg/ml from lipopolysaccharide of *Escherichia coli*, was added to the resultant cell suspension and incubated at 37° C. for 48 hours to induce a melanin formation-inhibitory protein.

The resultant cell culture was centrifuged to obtain a supernatant which was then concentrated with an ultrafiltration membrane having a molecular weight cut-off of 6,000–10,000. The resultant filtrate was dialyzed against 20 mM Tris-HCl buffer (pH 7.4) for 16 hours, and loaded on a "DEAE-5PW column", a column product commercialized by Tosoh Corporation, Tokyo, Japan, to adsorb thereon a melanin formation-inhibitory protein. The column was washed with the same fresh buffer, and the melanin formation-inhibitory protein adsorbed on the column was eluted therefrom with a gradient buffer that increased the concentration of saline from 0M to 0.5M. Active fractions were pooled and dialyzed against 25 mM Bis-Tris buffer (pH 7.1) for 16 hours, and the dialyzed pooled fractions containing an active protein were absorbed onto a "Mono P column" commercialized by Pharmacia LKB Biotechnology, Uppsala, Sweden, and eluted from the column with a gradient buffer that decreased the pH from 7 to 5, followed by recovering fractions containing the active protein. About 2 mg of a purified product was recovered from 100L of the above-mentioned supernatant.

The physicochemical properties of the present melanin formation-inhibitory protein were studied with the purified product.

(1) Molecular weight

In accordance with the method of Laemmli, *Nature*, Vol.227, pp.680–685 (1970), the purified product was subjected to SDS-PAGE. After electrophoresis, the resultant gel was sliced into pieces 2 mm wide, to which 250 μl of Eagle's minimum essential medium supplemented with 10 v/v % fetal calf serum, were added in total and soaked for 16 hours at 4° C. to extract a melanin formation-inhibitory protein. The activity of each extract from the sliced gels was determined using the following method. The results are shown in FIG. 1. In this figure, the numbers given on the x-axis (abscissa) indicate the gel numbers of the sliced gels; and those on the y-axis (ordinate) indicate the degrees in black of B-16 cells. FIG. 1 shows that a melanin formation-inhibitory protein is present in fractions having a low degree of black. As evident from FIG. 1, an active peak was observed in a part of the gel containing a protein with a relatively-low mobility. The molecular weight of the melanin formation-inhibitory protein was found to be 90,000±20,000 when determined in comparison with the relative mobilities of marker proteins;

(2) Isoelectric point

It was found that the purified product has a pI of 5.5±0.5 by chromatofocusing using "Mono P column";

(3) Ultraviolet absorption spectrum

The purified protein exhibited the maximum absorption spectrum at a wavelength of around 280 nm on a "UV 250 spectrophotometer", a product of Shimadzu Corporation, Kyoto, Japan;

(4) Solubility in solvent

Soluble in water, physiological saline, phosphate buffer and Tris-HCl buffer;

(5) Activity

In accordance with the method in *Cancer Research*, Vol.42, pp.1994–2002 (1982), the melanin formation-inhibitory activity of the purified product was assayed: $4 \times 10^4$ B-16 cells and a muse melanoma cell, were suspended in a 25 cm$^2$ culture flask with 10 ml of Eagle's minimum essential medium supplemented with 10 v/v % fetal calf serum, and cultured at 37° C. under 5 v/v % $CO_2$ conditions. The cultivation was carried out for 5 days while replacing the medium with the fresh medium supplemented with a prescribed amount of the purified product at 0 and 3 days after initiation of the culture. After completion of the culture, the resultant cells, grown on the inner walls of the culture flask, were washed with phosphate buffer (pH 7.2) supplemented with 0.8 w/v % salt, added, and with trypsin and ethylenediamine tetraacetic acid (EDTA) to detach the cells from the walls, for recovery by filtration. The cells, which were recovered on a filter paper were dried and then measured by a densitometer in order to determine the reflection absorption (degree of black) at a wavelength of 500 nm. Based on the above-mentioned method, one unit of melanin formation-inhibitory activity was defined as the activity observed when the absorbance in a test group was lowered to ½ of the absorbance in a control group. With a solution containing 2 μg/ml of purified protein, 30 units/ml of melanin formation-inhibitory activity was determined to be present in this solution using the above-mentioned method.

(6) Stability of activity

Figure 2:
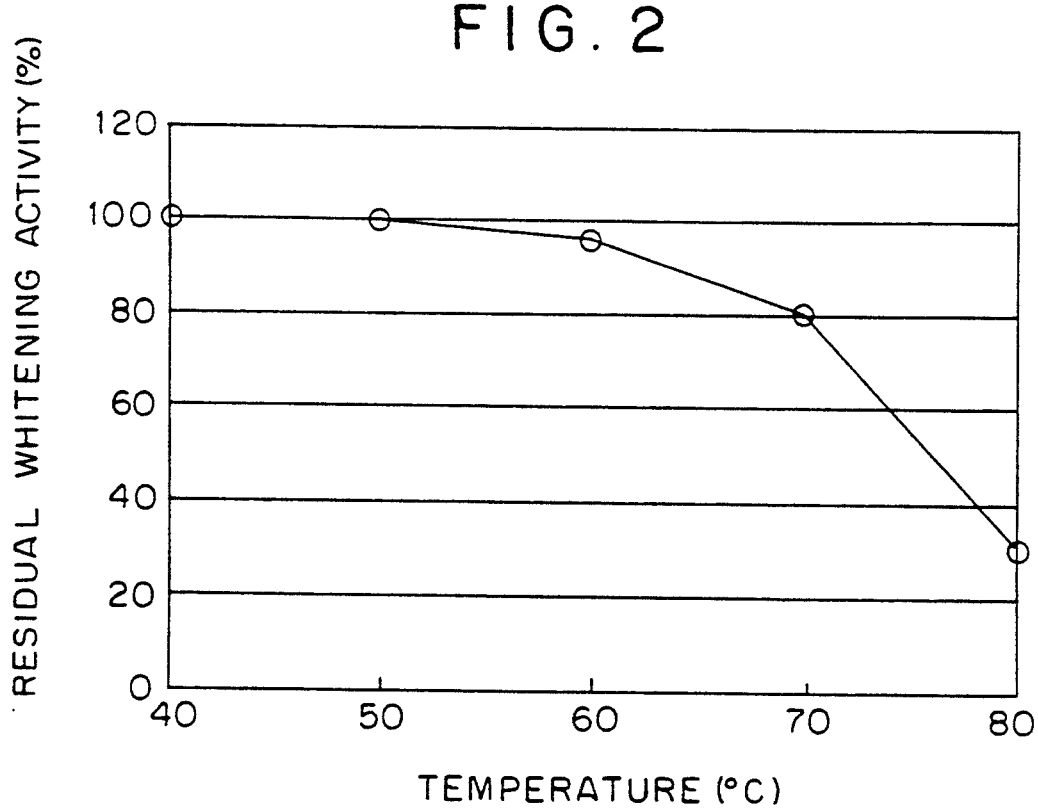
FIG. 2 shows a thermostability of the present melanin formation-inhibitory protein.

The purified protein was heated in solution (pH 7.4) to a temperature in the range of 40°–80° C. for 30 minutes, and then its activity was assayed with the above-mentioned method. The result is shown in FIG. 2. As evident from FIG. 2, the purified product is inactivated at a temperature of 80° C. or higher. No substantial loss of activity was observed in purified product after the storage at pH 7.4 and 4° C. for one month.

EXPERIMENT 2

Functional Mechanism of Melanin Formation-Inhibitory Protein

Intact B-16 cells used as a control and cells which had been whitened by treatment with the present melanin formation-inhibitory protein, were subjected to the following analyses:

(1) Quantitative analysis of melanin

According to the method of Ito et al., *Analytical Biochemistry*, Vol.144, pp.527–536 (1985), the eumelanin and pheomelanin in B-16 cells were quantitated. Table 1 shows the level of eumelanin in B-16 cells treated with the melanin formation-inhibitory protein was 1/15 of the level found in the control. This means that the degree of black in treated B-16 cells was lowered to 1/15 the level found in untreated B-16 cells. No significant change in the level of pheomelanin in B-16 cells was observed. In Table 1, the values in the columns for melanin content are given in melanin content (μg) per $1 \times 10^7$ B-16 cells.

(2) Assay of tyrosinase activity

Cells which had been treated with or without the purified protein were dipped by suspension in 5-fold volumes of 0.25M sucrose solution, followed by a cycle of repeated freezing and thawing. The resultant mixture was centrifugally separated into fractions of extract and sediment, followed by assaying the activity of each fraction in accordance with the method of Hamada et al., *British Journal of Dermatology*, Vol.86, pp.385–394 (1972). Enzymatic activity is expressed on the basis of the definition that one unit (U) of activity is that which decomposes one μmole of substrate per minute. As shown in Table 1, B-16 cells treated with the purified protein substantially lost their tyrosinase activity. The values of tyrosinase activity as presented in the column for tyrosinase activity in Table 1 are expressed as tyrosinase activity (mu) per $1 \times 10^7$ B-16 cells. No change was observed when the melanin formation-inhibitory protein was added to the tyrosinase assay system, which means that the present protein does not directly inhibit the tyrosinase activity.

(3) Determination of expression percentage of tyrosinase gene (mRNA)

The method used in the following experiment is a conventional technique described by M. Muramatsu, *Labomannual Genetic Engineering*, Published by Maruzen Co., Ltd., Tokyo, Japan (1988). RNAs of B-16 cells, treated with or without the purified protein, and prepared in the usual manner were subjected to agarose gel electrophoresis. Thereafter, the gel separated RNAs were transferred onto a cellulose membrane by the blotting technique. The RNAs transferred on the cellulose membrane were subjected to Northern hybridization by probing with a $^{32}$P-labelled cDNA of mouse tyrosinase as described in *The ENBO Journal*, Vol.7, pp.2,723–2,730 (1988). The resultant cellulose hybridization membrane was subjected to autoradiography with x-ray film. The expression percentage of the tyrosinase gene was evaluated based on the intensity of RNA bands hybridized with the probe. As shown in Table 1 no substantial difference in the expression percentage of tyrosinase gene was observed in the cells treated with and without the purified protein. In Table 1, the values in the column for the expression percentage of tyrosinase gene (mRNA) are expressed in relative values.

by the application to their grained skins. As evident from the above experiment, the present melanin formation-inhibitory protein has a strong melanin formation-inhibitory activity, i.e a sufficiently-high skin-whitening effect, as well as being safe at its effective dose.

Skin-whitening agents containing the present melanin formation-inhibitory protein can be administered at a dose of 0.01–10,000 units/day/adult, based on the amount of the protein, on a dry solid basis (d.s.b.); preferably, 0.01–1,000 units/day/adult in systematic administrations such as intramuscular injections and the like; and 0.01–10,000 units/day/adult in oral administrations such as with medicines taken orally, and percutaneous- and permucosal-administrations such as with the application milky lotions and creams. The dose can be changed depending on the suitable administration route and/or the patient's symptom. To prevent and/or treat local chromatosises such as chloasma, ephelis and sunburn, as well as systematic chromatosises such as addisonism, the melanin formation-inhibitory protein can be either used alone or suitably used as a skin-whitening agent in combination with biologically active substances, nutrient agents, bases, fillers, excipients and the like, for their final formulation such as in pharmaceuticals and cosmetics, as well as for their actual use.

The preferred preparations of the present melanin formation-inhibitory protein will be described in Examples A-1 and A-2.

EXAMPLE A-1

Melanin formation-inhibitory protein Purification of melanin formation-inhibitory protein from HL-60 cells (ATCC CCL 240)

A seed culture of HL-60 cells (ATCC CCL 240) was allowed to proliferate in a culture flask in a conventional manner. As in Experiment 1, an inducer was added to the proliferated cells to produce a melanin formation-inhibitory protein which was then purified and recovered. Approximately 100 μg of a purified specimen was obtained from 10L of culture supernatant. The melanin formation-inhibitory protein thus obtained has the same physicochemical properties as the protein in Experiment 1.

The product can be used as a skin-whitening agent in

TABLE 1

| | Tyrosinase | | | Content of melanin | |
|---|---|---|---|---|---|
| | Activity (mU/10$^7$ cells) | | Expression percentage of mRNA (%) | Eumelanin (μg/10$^7$ cells) | Pheomelanin (μg/10$^7$ cells) |
| | Extract | Residue | | | |
| Untreated | 1.8 | 4.2 | 100 | 59.8 | 0.76 |
| Treated | Below the limit of detection | 0.6 | 100 | 4.1 | 0.43 |

Based on these results, it is concluded that the present melanin formation-inhibitory protein does not directly inhibit melanin formation or tyrosinase activity, but rather inhibits a process occurring after the translation of a tyrosinase gene into a protein.

EXPERIMENT 3

Acute toxicity test

Acute toxicity of the melanin formation-inhibitory protein obtained in Experiment 1 was tested with 20-day old mice. The results found that the LD$_{50}$ of the protein is 150,000 units/kg or even higher when administered orally and intraperitoneally to mice, as well as pharmaceuticals such as injectables, orally administrable agents, externally administrable agents, and bath salts, as well as in cosmetics such as milky lotions, packs and creams; and exerts a relatively-high effect in the prevention and/or treatment for local chromatosises such as chloasma, ephelis and sunburn, as well as for systemic chromatosises such as addisonism.

EXAMPLE A-2

Melanin formation-inhibitory protein

A seed culture of RAMOS cells (ATCC CRL 1596) was allowed to proliferate in hamsters as similarly above in Experiment 1, and an inducer was added to the proliferated cells to produce a melanin formation-inhibitory protein followed by purifying and recovering the resultant protein. About one mg of purified protein was obtained from 50L of culture supernatant. The melanin formation-inhibitory protein thus obtained has the same physicochemical properties as the melanin formation-inhibitory protein in Experiment 1.

Like Example A-1, this product can be used in pharmaceuticals and cosmetics to exert a sufficiently-high effect in the prevention and/or treatment for chromatosises.

The following Examples B, B-1 and B-2 illustrate skin-whitening agents containing the present melanin formation-inhibitory protein as the effective ingredient.

EXAMPLE B-1

Injection

One thousand units of a melanin formation-inhibitory protein, obtained by the method in Experiment 1, was dissolved in 100 ml of a physiological saline containing 1 w/v % human serum albumin, and the resultant mixture was membrane filtered in the usual manner. Two ml aliquots of the resultant filtrate were distributed to vials, freeze dried, and then cap-sealed to form a lyophilized injectable. The product is used by dissolving in sterilized water prior to injection.

The product can be advantageously used as a skin-whitening agent in the prevention and/or treatment for local chromatosises such as chloasma, ephelis and sunburn, as well as for systemic chromatosises such as addisonism.

EXAMPLE B-2

Cosmetic (milky lotion)

To 100 ml of a base in the form of a milky lotion, prepared in usual manner, 1,000 units of a melanin formation-inhibitory protein prepared by the method in Experiment 1, was added and the resultant mixture was homogenized to obtain a milky lotion. The product can be advantageously used as a skin-whitening agent in the prevention and/or treatment for chromatosises such as chloasma, ephelis and sunburn.

As described above, the present invention is to establish a preparation of a novel melanin formation-inhibitory protein, which exerts a melanin formation-inhibitory activity without substantially inhibiting the enzymatic activity of tyrosinase and which inhibits the synthesis of tyrosinase in pigment cells, and to establish a skin-whitening agent containing the protein as the effective ingredient.

The present melanin formation-inhibitory protein exerts a relatively-strong melanin formation-inhibitory activity and skin-whitening effect when used as a skin-whitening agent in the prevention and/or treatment for local chromatosises such as chloasma, ephelis and sunburn in pharmaceuticals such as injectables, orally administrable agents, externally administrable agents and bath salts, as well as in cosmetics such as milky lotions, packs and creams.

The present melanin formation-inhibitory protein is safe and without side effects at its effective dose. This renders it industrially useful in the fields of pharmaceuticals and cosmetics.

While described as the preferred embodiments of the invention, it is understood that various modifications may be made, and the present invention is intended to cover in the claims all such modifications as fall within the scope of the invention.

We claim:

1. An isolated protein which has the following physicochemical properties:
    (1) Molecular weight
        $90,000 \pm 20,000$ on sodium dodecyl sulfate polyacrylamide gel electrophoresis (SDS-PAGE);
    (2) Isoelectric point
        $pI = 5.5 \pm 0.5$;
    (3) Ultraviolet absorption spectrum
        Exhibiting the maximum absorption spectrum at a wavelength of around 280 nm;
    (4) Solubility in solvent
        Soluble in water, physiological saline, phosphate buffer and Tris-HCl buffer;
    (5) Activity
        Exerting a melanin formation-inhibitory activity in pigment cells; and
    (6) Stability of activity
        Inactivated in water (pH 7.4) at 80° C. for 30 minutes; Stable in water (pH 7.4) at 4° C. for one month.

2. The an isolated protein of claim 1, which exerts tyrosinase formation-inhibitory activity in pigment cells.

3. The an isolated protein of claim 1, which is derived from HPB-MLT cell line (FERM BP-2430).

4. A process for preparing a protein, which comprises:
    allowing HPB-MLT cell line (FERM BP-2430) capable of producing a protein to cultivate in a nutrient culture medium to form said protein, and
    recovering said protein from the resultant culture; said protein having the following physicochemical properties:
    (1) Molecular weight
        $90,000 \pm 20,000$ on sodium dodecyl sulfate polyacrylamide gel electrophoresis (SDS-PAGE);
    (2) Isoelectric point
        $pI = 5.5 \pm 0.5$;
    (3) Ultraviolet absorption spectrum
        Exhibiting the maximum absorption spectrum at a wavelength of around 280 nm;
    (4) Solubility in solvent
        Soluble in water, physiological saline, phosphate buffer and Tris-HCl buffer;
    (5) Activity
        Exerting a melanin formation-inhibitory activity in pigment cells; and
    (6) Stability of activity
        Inactivated in water (pH 7.4) at 80° C. for 30 minutes; Stable in water (pH 7.4) at 4° C. for one month.

5. The process of claim 4, wherein said protein exerts a tyrosinase formation-inhibitory activity in pigment cells.

6. A composition to prevent and treat local chromatosises and systemic chromatosises, which comprises an effective amount of a protein as an effective ingredient, said protein exerting a melanin-formation inhibitory activity and skin-whitening activity and having the following physicochemical properties:
    (1) Molecular weight—$90,000 +/- 20,000$ on sodium dodecyl sulfate polyacrylamide gel electrophoresis (SDS-PAGE);
    (2) Isoelectric point—$pI = 5.5 +/- 0.5$;

(3) Ultraviolet absorption spectrum—Exhibiting the maximum absorption spectrum at a wavelength of around 280 nm;
(4) Solubility in solvent—Soluble in water, physiological saline, phosphate buffer and Tris-HCl buffer;
(5) Activity—Exerting a melanin formation-inhibitory activity in pigment cells; and
(6) Stability of activity—Inactivated in water (pH 7.4) at 80° C. for 30 minutes; Stable in water (pH 7.4) at 4° C. for one month.

7. The composition of claim 6, which exerts a tyrosinase formation-inhibitory activity in pigment cells.

8. The composition of claim 6, which is in the form of a cosmetic or a pharmaceutical.

9. The composition of claim 6, wherein said protein is prepared by a process comprising:

allowing HPB-MLT cell line (FERM BP-2430) capable of producing said protein to cultivate in a nutrient culture medium to form said protein, and recovering said protein from the resultant culture.

* * * * *